United States Patent

Rao et al.

Patent Number: 5,714,632
Date of Patent: Feb. 3, 1998

[54] AZLACTONE-BASED SURFACTANTS

[75] Inventors: Prabhakara S. Rao, Maplewood; Larry R. Krepski, White Bear Lake; Terrance P. Smith, Woodbury, all of Minn.

[73] Assignee: Minnesota Mining And Manufacturing Company, St. Paul, Minn.

[21] Appl. No.: 558,003

[22] Filed: Nov. 13, 1995

[51] Int. Cl.$^6$ .................................. C07C 229/00
[52] U.S. Cl. .................. 562/450; 560/41; 560/44; 560/125; 560/169; 562/433; 562/507; 562/565
[58] Field of Search ................... 562/565, 433, 562/450, 507; 560/44, 125, 170, 41, 169

[56] References Cited

U.S. PATENT DOCUMENTS

| | | | |
|---|---|---|---|
| 4,304,705 | 12/1981 | Heilmann et al. | 260/30.4 N |
| 4,451,619 | 5/1984 | Heilmann et al. | 525/379 |
| 4,485,236 | 11/1984 | Rasmussen et al. | |
| 4,597,794 | 7/1986 | Ohta et al. | 106/20 |
| 4,639,286 | 1/1987 | Rasmussen et al. | 156/307.3 |
| 4,663,184 | 5/1987 | Hegel | |
| 4,699,843 | 10/1987 | Charbonneau et al. | 428/355 |
| 4,705,889 | 11/1987 | Hendricks et al. | 562/564 |
| 4,931,582 | 6/1990 | Heilmann et al. | 560/172 |
| 4,988,602 | 1/1991 | Jongewaard et al. | 430/115 |
| 5,071,578 | 12/1991 | Ohkubo et al. | |
| 5,081,197 | 1/1992 | Heilmann et al. | 526/260 |
| 5,085,698 | 2/1992 | Ma et al. | 106/20 |
| 5,091,489 | 2/1992 | Heilmann et al. | 526/90 |
| 5,149,806 | 9/1992 | Moren et al. | 544/72 |
| 5,159,105 | 10/1992 | Hansen et al. | |
| 5,194,623 | 3/1993 | Krepski et al. | 548/261 |
| 5,210,282 | 5/1993 | Flynn et al. | |
| 5,216,084 | 6/1993 | Francis et al. | 525/328.2 |
| 5,236,741 | 8/1993 | Zwiener et al. | |
| 5,243,012 | 9/1993 | Wicks et al. | |
| 5,268,473 | 12/1993 | Moren et al. | 544/72 |
| 5,284,512 | 2/1994 | Koskan et al. | 106/416 |
| 5,292,514 | 3/1994 | Capecchi et al. | 424/422 |
| 5,336,742 | 8/1994 | Heilmann et al. | 526/260 |

FOREIGN PATENT DOCUMENTS

| | | |
|---|---|---|
| 0 449 488 | 10/1991 | European Pat. Off. |
| 0 573 860 | 12/1993 | European Pat. Off. |

OTHER PUBLICATIONS

Abstract of JP 5140059 (Patent Abstracts of Japan 1993).

*Primary Examiner*—Michael L. Shippen
*Attorney, Agent, or Firm*—Gary L. Griswold; Walter N. Kirn; John H. Hornickel

[57] ABSTRACT

A compound of the formula

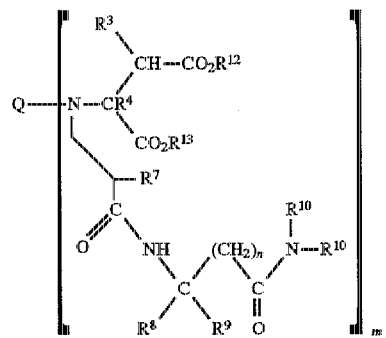

wherein
Q is an organic group of at least two carbon atoms having at least m substituents,
m is 1, 2, 3, 4, 5 or 6, and
n is 0 or 1.
$R^3$ is H or methyl,
$R^8$ and $R^9$ are independently hydrogen, alkyl group or aryl,
$R^{12}$ and $R^{13}$ are independently selected from the group consisting of an alkyl group or a cation, and
$R^{10}$ is independently selected from the group consisting of hydrogen, an alkyl group, aryl group, and highly-fluorinated alkyl group,
$R^4$ may be hydrogen or alkyl group, and
$R^7$ may be hydrogen or lower alkyl group, provides excellent stability to dispersions.

20 Claims, No Drawings

AZLACTONE-BASED SURFACTANTS

BACKGROUND OF THE INVENTION

1. Field of the Invention

The present invention relates to novel compounds which are useful as surfactants, dispersants and stabilizers. These compounds are particularly useful as dispersants for pigments and most particularly for hydrophobic pigments in aqueous-carrier toner dispersions.

2. Background of the Art

One significant problem in the storage or longevity of liquid-based solutions, emulsions and dispersions is the physical incompatibility of one or more components with each other or with the liquid carrier. This incompatibility of components in the composition is usually in the form of repulsive properties (e.g., such as that between hydrophilic and hydrophobic components) which can cause the ingredients to separate into distinct phases. Some of the phases may settle out of the liquid carrier and thereby remove the desired effect of the components of that phase from the composition. Undesired phase separation can readily cause significant variations in the properties of the composition from moment to moment during use.

A traditional method of reducing the effects of incompatibility of components within a liquid carrier or liquid-based system is to provide an additional component which is 'friendly' with at least two of the incompatible components. This additional component is usually referred to in the art as a surfactant, dispersant or stabilizer compound (hereinafter generally referred to as a dispersant). These dispersant compounds usually have two distinct sections or segments on the molecule, each one of the segments being selected to be compatible with a particular component of the liquid-based composition. By having compatibility with two incompatible or marginally compatible ingredients, the dispersant acts as a bridge between those ingredients, loosely ties them together, and thus stabilizes them in the liquid based composition.

The difficulty in the use of dispersants is that not all dispersants are useful for all incompatible materials. The nature of the incompatibility varies in different systems, the chemical or physical nature of incompatible ingredients may have unique attributes, and the dispersants may have properties that would be adverse to the needs of the composition. For example, in liquid toner compositions which require specific charge levels and exact color renditions, the use of dispersants with a significant charge or color would be undesirable.

Typically useful polymeric dispersants have a relatively low molecular weight (e.g., 10,000) and are block copolymers which contain a hydrophobic segments to interact with the organic pigment surface (which is generally hydrophobic) and a hydrophilic segment to provide water dispersibility.

U.S. Pat. No. 4,485,236 shows azlactone-functional compounds. These compounds are suggested for ring opening reactions with nucleophilic groups (e.g., amines and polyamines) on col. 7, lines 27–30. Other reactions of nucleophilic group substituted compounds with alkenyl azlactones are shown in column 4. The nucleophilic group-substituted compounds may contain other catenary or dependent groups, including ester groups (col. 4, lines 40–58).

U.S. Pat. Nos. 5,243,012 and 5,236,741 disclose polyurethane and polyurea coatings and polyaspartic esters useful in forming those compounds. The polyaspartic esters shown in formula (I) of both patents can provide stable coating compositions and are reacted with isocyanates to form the coatings. No other reactants other than the isocyanates are claimed in the patents.

SUMMARY OF THE INVENTION

The present invention relates to novel dispersants which are particularly useful in stabilizing dispersions of pigments in liquid carrier media, especially in aqueous carriers for toners. The dispersants of the present invention may be the reaction products of polyamino acid, amino acid salts, or amino acid esters compounds and alkenyl azlactones (including vinyl azlactones). Both the substituents on the amino acid compound and the alkenyl azlactone may be selected to tailor the physical properties of the dispersant to the needs of particular combinations of surfaces and/or compounds which are to be stabilized within a dispersion. The relatively low molecular weight of the dispersants of the present invention provide an excellent degree of isotropic dispersant, particularly as compared to polymeric dispersant.

DETAILED DESCRIPTION OF THE INVENTION

The present invention relates to the preparation, formulation and composition of novel dispersants, particularly for use in stabilizing dispersions of components in liquid carriers. The dispersants of the invention are particularly useful in stabilizing dispersions of hydrophobic materials (e.g., pigments, ferromagnetic materials, abrasive particulates, and the like) in liquid dispersions, especially aqueous dispersions. The dispersants of the present invention may be the reaction products of N-substituted amino acid compounds (particularly aspartic acid esters) and alkenyl azlactones. Both the substituents on the N-substituted amino acid and the alkenyl azlactone may be selected to tailor the physical properties of the dispersant to the needs of particular combinations of surfaces and/or compounds which are to be stabilized within a dispersion.

The dispersants of the invention are most conveniently synthesized by the reaction of N-substituted amino acid esters with alkenyl azlactones, each of the two reactants being selected with a variety of alternative substituents so as to contribute to the overall specifics of properties in the final dispersant product. By selection of substituent groups, the degree of hydrophilicity or hydrophobicity for the end segments of the compound may be varied and controlled.

The surfactants of this invention are prepared by reacting N-substituted amino acid esters or homologues of N-substituted amino acid esters with alkenyl azlactones. Non-limiting examples of starting N-substituted amino acid esters would be esters of the following N-substituted amino acids: N-methylglycine, N-butyl-2-)3,5,7-trimethyl-1-adamantyl)glycine, N-phenylglycine, N-(2-cyanoethyl) glycine, N- phenylglycine, N-methyl-(l)-alanine, N-methyl-(d)-alanine, N- methyl-(dl)-alanine, 2-(methylamino) isobutyric acid, N-methyl-(d)-aspartic acid, N-benzyl-(dl)-aspartic acid, sarcosine, iminodiacetic acid, ethylene-N,N'-diacetic acid, Imidazole-4,5-dicarboxylic acid, L-thiazolidine-4-carboxylic acid, L-thiazolidine-4-carboxylic acid, 3,4-dehydro-(dl)-proline, Pyrrole-2-carboxylic acid, (dl)-proline, diglycine, N-methyl-(dl)-glutamic acid, N-methyl-(d)-phenylalinine, N-methyl-(l)-leucene, N-α-methyl-(l)-histidine, H-meval-OH, 2,2'-(ethylenediamino)-dibutyric acid, N-cyclohexyl-β-alanine, (±)-cis-2,3-piperidine dicarboxylic acid, cis-2,5-piperidine dicarboxylic acid, carboxyethyl-gamma-amino-butyric acid, ethylenediamine-N,N'-dipropionic acid, (±)-cis-2,3-piperazine carboxylic acid, L-trans-pyrollidine-2,4-dicarboxylic acid, 2,2'-iminobis(1-cyclopentanecarboxylic acid), cis-2-(ethylamino)-1-1-cyclohexanecarboxylic acid. The reaction of amino acids which contain primary amines, alcohols or thiols, (i.e., such as lysine, serine, or cysteine) with the alkenyl azlactones would result in a ring opened product, not the desired Michael adduct; however, appropriately protected derivatives of these amino acids would be suitable. Methods for protecting amino acids are well known in the art and are used extensively in the preparation of peptides (see, for example, R. Barker, "Organic Chemistry of Biological Compounds," Prentice-Hall, Englewood Cliffs, N.Y., 1971, pp 76–84.) A preferred embodiment is derivatives of aspartic esters.

"Aspartic acid esters" are hereinafter defined as the reaction products of a primary amine with an optionally substituted maleic or fumaric ester as shown in the following scheme:

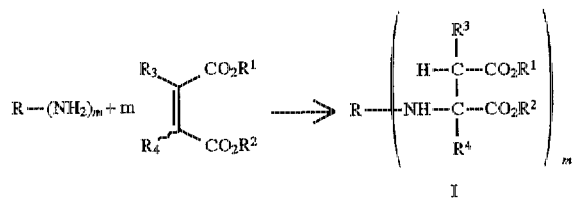

where
R is an alkyl, aryl, or aralkyl group obtained by the removal of primary amino groups from alkyl, aryl, or aralkyl amines,
m=1 to 6,
$R^1$ and $R^2$ are alkyl, aryl, or aralkyl, and $R^3$ and $R^4$ are hydrogen or lower alkyl.

Examples of R include monovalent groups such as methyl, ethyl, butyl, octyl, hexadecyl, octadecyl, phenyl, and phenethyl which are obtained upon removal of the amino groups from the corresponding primary amines, divalent groups which are obtained after the removal of the primary amino groups from diamines such as 1,4-diaminobutane, 1,6-diaminohexane, 1,12-diaminododecane, 1,3-diaminopentane, 2-methyl- 1,5-pentanediamine, 2,2,4- and 2,4,4-trimethyl- 1,6-diaminohexane, 1-amino-3,3,5-trimethyl-5-aminomethylcyclohexane, 4,4'-diaminodicyclohexylmethane, 3,3-dimethyl-4,4'-diaminodicyclohexylmethane, and 4,4'-diaminodicyclohexylmethane. Other examples of R include the groups which are obtained after the removal of the primary amino groups from primary amines which contain secondary or tertiary amino groups such as N-ethylethylenediamine, N,N-dibutylethylenediamine, 3,3'-iminobispropylamine, triethylenetetramine, and spermidine. Other examples of R include the groups which are obtained after the removal of the primary amino groups from polyether amines such as 4,7,10-trioxa-1,13-tridecanediamine and amine terminated polyethers such as those marketed under the Jeffamine trademark by the Huntsman Corporation, Salt Lake City, Utah. An example of a trivalent R group is the group which is obtained after the removal of the primary amino groups from tris(2-aminoethyl)amine.

Examples of $R^1$ and $R^2$ include methyl, ethyl, propyl, n-butyl, t-butyl, octyl, hexadecyl, tridecafluoro-1-octanol, and benzyl.

Examples of $R^3$ and $R^4$ include hydrogen, methyl, and ethyl.

Other examples of suitable amines and the aspartic esters derived from them are described in U.S. Pat. Nos. 5,243,012 and 5,236,741.

One structural formula which defines certain of the useful amino acid ester compounds (including aspartic ester compounds) which may be used in the synthetic reactions of the present invention to produce useful dispersants is formula (II) as follows:

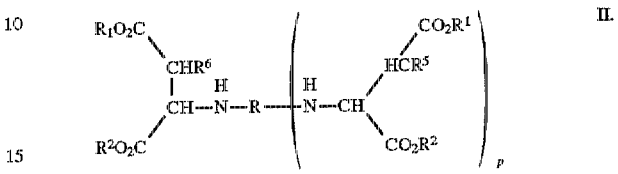

wherein
R is a monovalent, divalent, or polyvalent (e.g., p+1 valent) organic group of at least two carbon atoms, preferably R is selected from alkylene of 2 to 20 carbon atoms (including O, S, N bridging atoms in the main chain), including cycloalkylene and aryl groups Aryl groups preferably have from 5 to 20 atoms in the core group bridging the two nitrogen atoms.

$R^1$ and $R^2$ are independently alkyl groups, preferably lower alkyl or 1 to 4 carbon atoms, and most preferably 2 carbon atoms, $R^5$ and $R^6$ may be hydrogen or lower alkyl of 1 to 4 carbon atoms, and p may be 0, 1, 2, or 3, preferably 0 or 1.
Preferably, the compounds are symmetrical from a synthetic standpoint.

The alkenyl azlactone compounds which are useful in the practice of the present invention may be partially defined by the following formula which represents the preferred azlactones useful in the present invention:

III. Alkenylazlactone

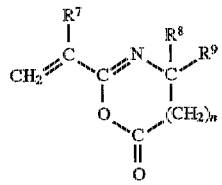

wherein
$R^7$ is hydrogen or methyl group,
$R^8$ and $R^9$ are independently hydrogen, alkyl group or aryl, with preferably only one of $R^8$ and $R^9$ being aryl (preferably phenyl), and
n is 0 or 1. When $R^7$ is H, the compounds are vinyl azlactones, and when $R^7$ is methyl, the compounds are alkenyl azlactones.

Nonlimiting examples of alkenyl azlactones and their syntheses are disclosed in U.S. Pat. Nos. 4,304,705; 5,081,197; and 5,091,489, incorporated herein by reference. Suitable alkenyl azlactones include;

2-ethenyl-1,3-oxazolin-5-one, 2-ethenyl-4-methyl-1,3-oxazolin-5-one, 2-isopropenyl-1,3-oxazolin-5-one, 2-isopropenyl-4-methyl-1,3-oxazolin-5-one, 2-ethenyl-4,4-dimethyl-1,3-oxazolin-5-one, 2-isopropenyl-4,4-dimethyl-1,3-oxazolin-5-one, 2-ethenyl-4-methyl-4-ethyl-1,3-oxazolin-5-one, 2-isopropenyl-4-methyl-4-butyl-1,3-oxazolin-5-one,
2-ethenyl-4,4-dibutyl-1,3-oxazolin-5-one,
2-isopropenyl-4-methyl-4-dodecyl-1,3-oxazolin-5-one,
2-isopropenyl-4,4-diphenyl-1,3-oxazolin-5-one,
2-isopropenyl-4,4-pentamethylene-1,3-oxazolin-5-one,
2-isopropenyl-4,4-tetramethylene-1,3-oxazolin-5-one,
2-ethenyl-4,4-diethyl-1,3-oxazolin-5-one,
2-ethenyl-4-methyl-4-nonyl-1,3-oxazolin-5-one,
2-isopropenyl-4-methyl-4-phenyl-1,3-oxazolin-5-one,
2-isopropenyl-4-methyl-4-benzyl-1,3-oxazolin-5-one,
and 2-ethenyl-4,4-pentamethylene-1,3-oxazolin-5-one, The preferred 2-alkenyl azlactones include 2-ethenyl-4,4-dimethyl-1,3-oxazolin-5-one (referred to herein as VDM) and 2-isopropenyl-4,4-dimethyl-1,3-oxazolin-5-one (referred to herein as IDM).

The N-substituted amino acid esters (particularly the aspartic esters) and the alkenylazlactones are reacted, followed by a ring opening compound for the azlactone. This ring opening compound may be any free hydrogen donating compound (e.g., thioalcohol, alcohol, or amine for example) and is preferably an amine.

The aspartic esters of Formula I and the alkenyl azlactones of Formula II are reacted together to produce a new azlactone material of Formula III. This compound of Formula III is the result of a Michael-addition of the nitrogen atoms of the aspartic ester of Formula I to the carbon-carbon double bond of the alkenyl azlactone of Formula II. More details and other examples of this Michael addition of alkenyl azlactones are disclosed in U.S. Pat. Nos. 4,485,236; 4,699,843; 5,149,806; 5,194,623; 5,268,473; and 5,292,514, incorporated herein by reference.

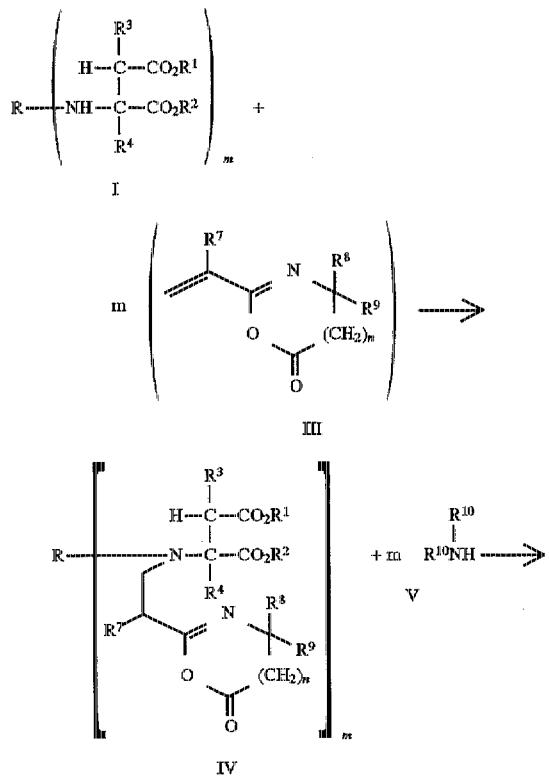

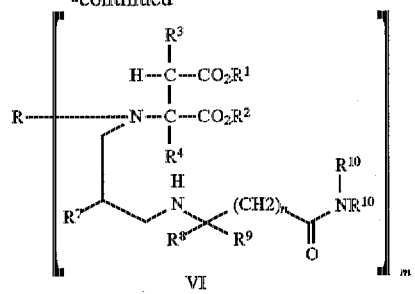

The next step in the preparation of the dispersants of the present invention involves a ring opening reaction of the azlactone rings of the compound of Formula III. The ring opening compound may be any free hydrogen donating nucleophile (e.g., alcohol, mercaptan, or amine) and is preferably an amine. This ring opening reaction of azlactones is well known in the art and exemplified in more detail in U.S. Pat. Nos. 4,451,619; 4,931,582; 5,216,084; and 5,336,742, incorporated herein by reference, as well as in previously noted U.S. Pat. No. 5,194,623.

Preferred examples of amines useful in the practice of the present invention as ring opening compounds for use with the vinylazlactones in the formation of products of the present invention are exemplified by Formula (V).

V. a) $NH_2R^{10}$, e.g., $NH(R^{10})_2$ wherein $R^{10}$ is independently hydrogen, an alkyl group, aryl group, linear or cyclic versions of heteroatom chains such as $(CH_2-CH_2-X)p$ where X is O, S, NH, or the like and p is the number of repeating units, oligomeric groups (e.g., polyoxyalkylene of 100 to 10,000 MW), fluorinated alkyl (e.g., highly fluorinated alkyl groups of 20 to 76% by weight fluorine, as where at least 40% of the hydrogen atoms have been replaced by fluorine), The oligomeric group may also have water-soluble segments such as acrylamides, 2-acrylamido-2-methylpropane sulfonic acid, N,N-dimethylacrylamide (meth)acrylic acid, and the like. The length of $R^{10}$ may be up to MW 500,000 if the dispersant is to be used in organic solvents for dispersing pigments in paints or other coating formulations.

Ring opening reactions of the new azlactone materials of formula III produce the novel dispersants of the present invention.

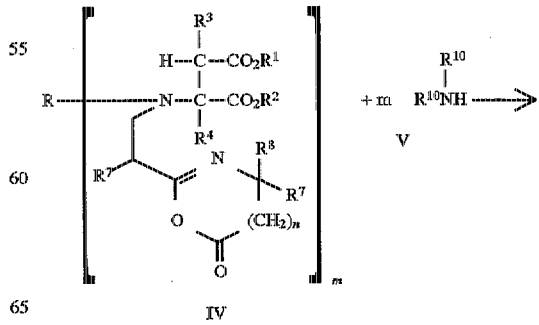

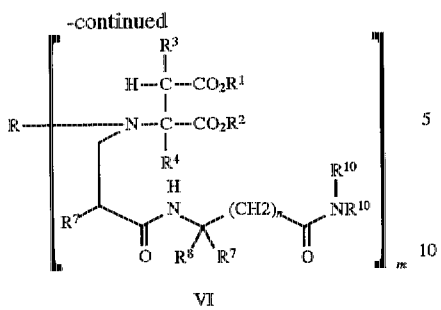

VI

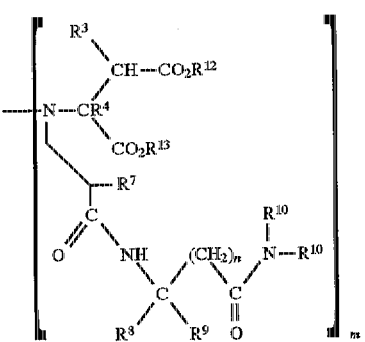

VIII

The compound of Formula VI may be treated with a hydroxide salt such as lithium hydroxide, sodium hydroxide, potassium hydroxide, ammonium hydroxide, or a tetrasubstituted ammonium hydroxide such as tetramethylammonium hydroxide or tetrabutylammonium hydroxide to cause hydrolysis of one or more of the ester groups $CO_2R^1$ and $CO_2R^2$. In some instances, it may be desirable to remove the groups $R^1$ and $R^2$ by other methods well known in the art, for example, hydrogenolysis of a benzyl ester or acid catalyzed removal of a tertiary butyl ester. This treatment of the compounds of Formula VI produces the dispersant compounds of the present invention of Formula VII, wherein $R^{12}$ and $R^{13}$ are independently $R^1$ and $R^2$, respectively, or a cation such as a proton, lithium, sodium, potassium, ammonium, or tetraalkyl ammonium such as tetramethylammonium or tetrabutylammonium (e.g., $COO^-Li^+$).

The formula which represents some of the preferred dispersants of the present invention may be written as follows in Formula (VII):

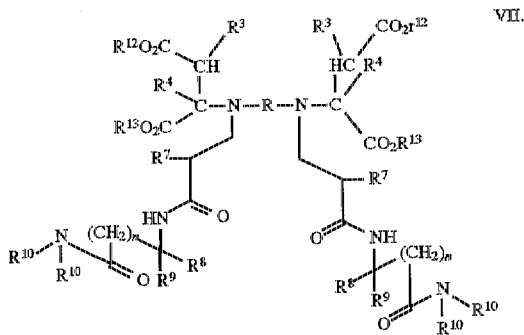

VII.

wherein n, R, $R^3$, $R^4$, $R^7$, $R^8$, $R^9$, and $R^{10}$ are as previously defined $R^{12}$ and $R^{13}$ may be independently selected from an alkyl group to complete the esters on the compound or a cation to complete a salt with the COO group (which is then $COO^-$), and $R^{10}$ may be, for example, any group which completes an amine with —NH— such as alkyl group, aryl group, heterocyclic group, and highly-fluorinated alkyl as previously defined (including highly fluorinated cycloalkyl).

Where reactants other than amines are used to open the azlactone rings, the bridging —NH— group adjacent $R^{10}$ in formula VII would be replaced by such bridging groups as —S—, —O—, $NR^{14}$, and the like, where $R^{14}$ completes such secondary amino group.

The preferred dispersant compounds alternatively may also be represented by the formula wherein Q is an organic group having m substituents represented by the bracketed information, such as divalent alkanes, 1,4-butane, 1,6-hexane, 2,2,4-trimethyl-1,6-hexane, 3,3,5-trimethyl-1,6-cyclohexane, 3,3-dimethyl-4,4-dicyclohexyl methane, 2-methyl pentane (1,5 attachment), butane, pentane, hexane, etc.

m is 1, 2, 3, 4, 5 or 6, and preferably is 1, 2, or 3, and most preferably 2, n, $R^3$, $R^4$, $R^7$, $R^8$, $R^9$, $R^{12}$, and $R^{13}$ are as defined above, and preferably $R^4$ and $R^5$ independently represent hydrogen or alkyl groups, preferably lower alkyl groups of 1 to 4 carbon atoms, most preferably 1 or 2 carbon atoms.

In the practice and the field of the present invention, substitution of the groups which are not directly involved in the reaction steps forming the compounds of the present invention may be substituted to meet desired physical property requirements in the final dispersants. This is not only allowable, but also in the formation of tailored dipsersants, this may be highly desirable or essential. Where individual substituents may tolerate such broad substitution, they are referred to as groups. Where no substitution is allowed, they are referred to as moieties. For example, alkyl group may allow for ester linkages or ether linkages, unsubstituted alkyl, alkyl with such useful substitution as halogen, cyano, carboxylic ester, sulfonate esters or salts, and the like. Where the term alkyl or alkyl moiety is used, that term would include only unsubstituted alkyl such as methyl, ethyl, propyl, butyl, cyclohexyl, isooctyl, dodecyl, etc.

These and other attributes of the present invention will be shown by the following, non-limiting examples of the practice of the present invention.

EXAMPLES 1–5

A 32 oz. glass jar was charged with 138.2 g of Bayer aspartic ester (#XP7059E) and 83.5 g of vinyldimethyl azlactone (available from SNPE, Princeton, N.J.). The jar was sealed and placed in an oven at 60° C. for 3 days. After this period, the jar was removed from the oven, cooled, opened, and 0.60 mol of the amine (n-butylamine for Example 1, n-octylamine for Example 2, n-dodecylamine for Example 3, n-octadecylamine for Example 4, or phenethylamine for Example 5) was added in portions over a 30 min. period (exothermic reaction). The jar was sealed and placed back in a 60° C. oven overnight. After this period, ethanol (200 mL) was added to dissolve the product, and 5 Normal sodium hydroxide solution (230 mL) added. The reaction mixture was agitated with brief warming on a steam bath to affect solution, then allowed to stand overnight at room temperature. Most of the ethanol was removed at reduced pressure and the remaining aqueous solution was extracted with 3 250 mL portions of ethyl acetate. (For Example 4, the ethyl acetate extraction step was omitted.) The aqueous solution was rotovapped again at reduced pressure to remove any remaining organic solvent. Percent solids were determined by heating a 2–3 g sample at 110° C. for 2 hours. Sufficient water was then added to make a 50% solution of the desired product in water.

EXAMPLE 6

A 16 oz. glass jar was charged with 30.3 g (0.25 mol) of phenethylamine (available from Aldrich Chemical Co.) and 43.0 g (0.25 mol) of diethylmalonate (available from Aldrich Chemical Co.) The jar was sealed and placed in an oven at 60° C. for 2 days. After this period, the jar was removed from the oven, cooled, opened, and 34.8 g (0.25 mol) of vinyldimethyl azlactone (available from SNPE, Princeton, N.J.) were added. The jar was sealed and placed back in an oven at 60° C. for 3 days. After this period, the jar was removed from the oven, cooled, opened, and 18.3 g (0.25 mol) of n-butylamine were added in portions over a 30 min. period (exothermic reaction). The jar was sealed and placed back in a 65° C. oven overnight. After this period, ethanol (100 mL) was added to dissolve the product, and a solution of 20 g (0.50 mol) of sodium hydroxide in 100 mL of water was added. The reaction mixture was agitated with brief warming on a steam bath to affect solution, then allowed to stand overnight at room temperature. Most of the ethanol was removed at reduced pressure and the remaining aqueous solution was extracted with 3 150 mL portions of ethyl acetate. The aqueous solution was rotovapped again at reduced pressure to remove any remaining organic solvent. Percent solids were determined by heating a 2–3 g sample at 110° C. for 2 hours. Sufficient water was then added to make a 50% solution of the desired product in water.

EXAMPLE 7

A 16 oz. glass jar was charged with 21.9 g (0.15 mol) of tris(2-aminoethyl)amine (available from Aldrich Chemical Co.) and 77.5 g (0.45 mol) of diethylmalonate (available from Aldrich Chemical Co.) The jar was sealed and placed in an oven at 60° C. for 2 days. After this period, the jar was removed from the oven, cooled, opened, and 62.6 g (0.45 mol) of vinyldimethyl azlactone (available from SNPE, Princeton, N.J.) were added. The jar was sealed and placed back in an oven at 60° C. for 3 days. After this period, the jar was removed from the oven, cooled, opened, and 32.9 g (0.45 mol) of n-butylamine were added in portions over a 30 min. period (exothermic reaction). The jar was sealed and placed back in a 65° C. oven overnight. After this period, ethanol (125 mL) was added to dissolve the product, and a solution of 36 g (0.90 mol) of sodium hydroxide in 100 mL of water was added. The reaction mixture was agitated with brief warming on a steam bath to affect solution, then allowed to stand overnight at room temperature. Most of the ethanol was removed at reduced pressure and the remaining aqueous solution was extracted with 4 150 mL portions of ethyl acetate. The aqueous solution was rotovapped again at reduced pressure to remove any remaining organic solvent. Percent solids were determined by heating a 2–3 g sample at 110° C. for 2 hours. Sufficient water was then added to make a 50% solution of the desired product in water.

EXAMPLES 8 AND 9

A 16 oz. glass jar was charged with 23.0 g of Bayer aspartic ester #XP 7059E and 13.9 of vinyldimethyl azlactone (available from SNPE, Princeton, N.J.). The jar was sealed and placed in an oven at 65° C. for 3 days. After this period, the jar was removed from the oven, cooled, opened, and 0.10 mol of the amine (Jeffamine™ M-600 {O(2-aminopropyl)-O'-(methoxyethyl)polypropylene glycol 500] for Example 8, or Jeffamine™ M-1000 [O-(2-aminopropyl)-O'-(2-methoxyethyl)copoly(ethylene)propylene glycol 900] for Example 9, both available from Fluka Chemical Corp., Konkonkoma, N.Y.) was added. The jar was sealed and placed back in a 70° C. oven for 2 days. The product was used directly without any further purification.

Examples of dispersants of the present invention are shown in Table I below.

TABLE I

| Ex. | Q | $R^3$ | $R^4$ | $R^7$ | $R^8$ | $R^9$ | $R^{10[1]}$ | $R^{12}$ | $R^{13}$ | m | n |
|---|---|---|---|---|---|---|---|---|---|---|---|
| 1 | Q* | H | H | H | $CH_3$ | $CH_3$ | $C_4H_9$ | Na | Na | 2 | 0 |
| 2 | Q* | H | H | H | $CH_3$ | $CH_3$ | $C_8H_{17}$ | Na | Na | 2 | 0 |
| 3 | Q* | H | H | H | $CH_3$ | $CH_3$ | $C_{12}H_{25}$ | Na | Na | 2 | 0 |
| 4 | Q* | H | H | H | $CH_3$ | $CH_3$ | $C_{18}H_{37}$ | Na | Na | 2 | 0 |
| 5 | Q* | H | H | H | $CH_3$ | $CH_3$ | $CH_2CH_2C_6H_5$ | Na | Na | 2 | 0 |
| 6 | $C_6H_5CH_2CH_2$ | H | H | H | $CH_3$ | $CH_3$ | $C_4H_9$ | Na | Na | 1 | 0 |
| 7 | $N(CH_2CH_2)_3$ | H | H | H | $CH_3$ | $CH_3$ | $C_4H_9$ | Na | Na | 3 | 0 |
| 8 | Q* | H | H | H | $CH_3$ | $CH_3$ | R** | $C_2H_5$ | $C_2H_5$ | 2 | 0 |
| 9 | Q* | H | H | H | $CH_3$ | $CH_3$ | R*** | $C_2H_5$ | $C_2H_5$ | 2 | 0 |

*(The aspartic ester used in the preparation of the dispersant of these examples was Bayer Desmophen ™ XP7059E, available from the Bayer Corporation, Pittsburgh. Q* is believed to be a short chain alkyl group.)
**The amine used in the ring opening reaction to prepare dispersant of Example 8 was Jeffamine ™ M-1000 [O-(2-aminopropyl)-O'-(methoxyethyl)polypropylene glycol 500] (available from Fluka Chemical Corp. Ronkonkoma, NY).
***The amine used in the ring opening reaction to prepare dispersant of Example 9 was Jeffamine ™ M-1000 [O-(2-aminopropyl)-O'-(2-methoxyethyl)copoly(ethylene, propylene glycol 900] (available from Fluka Chemical Corp. Ronkonkoma, NY).
[1]Only 1 $R^{10}$ is other than H in these examples.

The dynamic surface tension data in Table 2 were obtained by measuring the pressure differential of the test solution between two tubes of different radii using a Sensadyne Model 6000 Surface Tensiometer with an instrument resolution of 0.1 mN/meter (dynes/cm).

TABLE 2

Dynamic Surface Tension Data
[Potential Surface Active Agents and Dispersants]
Dynamic Surface Tension [dynes/cm]* at 23–24.4° C.

| Concentration Wt. % in Water | Azlactone Derivative | | | | | |
|---|---|---|---|---|---|---|
| | Ex. 1 | Ex. 2 | Ex. 5 | Ex. 6 | Ex. 7 | Ex. 4 |
| 0.25 | | 50.8 | | | | |
| 0.5 | 65.9 | 44.1 | 57 | 60.6 | | Emulsion Particle Size = ~350 nm |
| 1 | 64.9 | 38.6 | 52.7 | 56.6 | | Emulsion Particle Size = ~350 nm |
| 2 | 61.7 | 36.7 | 53.5 | 52 | | Emulsion Particle Size = ~350 nm |
| 3 | 59.7 | 36.7 | 51.1 | 49.3 | | Emulsion Particle Size = ~350 nm |
| 4 | 58.9 | 37.4 | 48.3 | 48.9 | 61 | |
| 8 | 54.8 | 38.2 | | | | |
| 12 | 52 | 37.1 | 46.5 | 42.8 | 52.7 | |
| 16 | 48.9 | 36.3 | | | | |
| 20 | 47.9 | 38.5 | | | | |
| *pH of 4% Solutions | 11.4 | 10 | 10.6 | 9.85 | 11 | |

Surface tension of water = 71.4–72.6 in the range 22 to 21° C. (repeat measurements)

EXAMPLE 10

The most surface active of the azlactone derivatives, namely that of Example 2, was tested for its emulsifying action. Two systems were used for testing. The first system is a 20% mixture of the monomer isobornyl acrylate (IBA, an example of a highly hydrophobic monomer) in water and the other, a 20% mixture of methylmethacrylate monomer (MMA, an example of a hydrophilic, but sparingly water-soluble monomer). About 4–5 percent of the dispersant of Example 2 yielded stable emulsions of the monomers in water under stirred conditions. The size of the droplets of IBA was ~500–600nm and that of the MMA was ~230–240 nm. This azlactone derivative is therefore suitable for use in the emulsion polymerization of a wide selection of monomers.

What is claimed:
1. A compound of the fomula

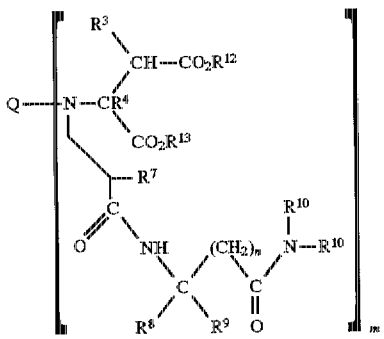

wherein
Q is an organic group of at least two carbon atoms having m valencies and m substituents of the group within the brackets,
m is 1, 2, 3, 4, 5 or 6, and
n is 0 or 1,
$R^3$ is H or a methyl group,
$R^8$ and $R^9$ are, independently, hydrogen, an alkyl group or an aryl group,
$R^{12}$ and $R^{13}$ are independently selected from the group consisting of an alkyl group or a cation,
$R^{10}$ is selected from the group consisting of hydrogen, an alkyl group, an aryl group, and a highly-fluorinated alkyl group,
$R^4$ is hydrogen or an alkyl group, and
$R^7$ is hydrogen or a lower alkyl group.
2. The compound of claim 1 wherein Q is selected from a) alkylene of 2 to 20 atoms, including alkylene with O, S, N bridging atoms in the main chain, and b) aryl.
3. The compound of claim 1 wherein Q is alkylene of 2 to twenty carbon atoms.
4. The compound of claim 1 wherein Q is alkylene of 2 to 8 carbon atoms.
5. The compound of claim 1 wherein m is 2 or 3.
6. The compound of claim 3 wherein m is 2 or 3.
7. The compound of claim 3 wherein $R^{12}$ and $R^{13}$ are a lower alkyl group of 1 to 4 carbon atoms.
8. The compound of claim 7 wherein $R^3$, $R^7$ are hydrogen, and $R^8$ and $R^9$ are methyl.
9. The compound of claim 6 wherein $R^3$, $R^7$ are hydrogen, and $R^8$ and $R^9$ are methyl.
10. The compound of claim 1 wherein each $R^{10}$ is selected from hydrogen and alkyl of 2 to 32 carbon atoms.
11. The compound of claim 2 wherein each $R^{10}$ is selected from hydrogen and alkyl of 2 to 32 carbon atoms.
12. The compound of claim 7 wherein each $R^{10}$ is selected from hydrogen and alkyl of 2 to 32 carbon atoms.
13. A compound of the formula:

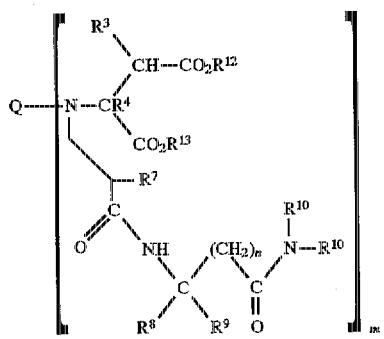

wherein
R is a monovalent, divalent, or polyvalent organic group having from 2 to 20 carbon atoms and having m valencies,
m is 1, 2, 3, 4, 5 or 6,
n is 0 or 1,
$R^3$ is H or a methyl group,
$R^8$ and $R^9$ are, independently, hydrogen, an alkyl group or an aryl group,
$R^{12}$ and $R^{13}$ are independently selected from the group consisting of an alkyl group or a cation,
$R^{10}$ is selected from the group consisting of hydrogen, an alkyl group, an aryl group, and a highly-fluorinated alkyl group,
$R^4$ is hydrogen or an alkyl group, and
$R^7$ is hydrogen or a lower alkyl group.
14. The compound of claim 13, wherein R includes O, S, or N bridging atoms in a main chain of R.

15. The compound of claim 13, wherein R is selected from the group consisting of alkylene, cycloalkylene, and aryl.

16. The compound of claim 15, wherein R is aryl, have from 5 to 20 carbon atoms in a core bridging two nitrogen atoms.

17. The compound of claim 16, wherein the compound is symmetrical from a synthetic standpoint.

18. The compound of claim 13, wherein m is 2 or 3.

19. The compound of claim 13, wherein $R^3$, $R^4$ and $R^7$ are hydrogen; $R^8$ and $R^9$ are $CH_3$; $R^{10}$ is $C_4H_9$; $R^{12}$ and $R^{13}$ are $Na^+$; m is 2; and n is 0.

20. The compound of claim 13, wherein $R^3$, $R^4$ and $R^7$ are hydrogen; $R^8$ and $R^9$ are $CH_3$; $R^{10}$ is $C_8H_{17}$; $R^{12}$ and $R^{13}$ are $Na^+$; m is 2; and n is 0.

* * * * *